United States Patent
Al Mayiah (10) Patent No.: US 10,806,952 B2
(45) Date of Patent: Oct. 20, 2020

(54) THERAPEUTIC ULTRASOUND APPARATUS AND METHOD

(71) Applicant: King Fahad Medical City (KFMC), Riyadh (SA)

(72) Inventor: Fares Al Mayiah, Riyadh (SA)

(73) Assignee: King Fahad Medical City (KFMC), Riyadh (SA)

( * ) Notice: Subject to any disclaimer, the term of this patent is extended or adjusted under 35 U.S.C. 154(b) by 279 days.

(21) Appl. No.: 15/114,753

(22) PCT Filed: Jan. 26, 2015

(86) PCT No.: PCT/GB2015/050167
§ 371 (c)(1),
(2) Date: Jul. 27, 2016

(87) PCT Pub. No.: WO2015/110836
PCT Pub. Date: Jul. 30, 2015

(65) Prior Publication Data
US 2016/0339273 A1 Nov. 24, 2016

(30) Foreign Application Priority Data

Jan. 27, 2014 (GB) .................................. 1401345.2

(51) Int. Cl.
*A61N 7/02* (2006.01)
*A61N 7/00* (2006.01)
*A61B 17/00* (2006.01)

(52) U.S. Cl.
CPC ...... *A61N 7/02* (2013.01); *A61B 2017/00172* (2013.01); *A61B 2017/00185* (2013.01);
(Continued)

(58) Field of Classification Search
None
See application file for complete search history.

(56) References Cited

U.S. PATENT DOCUMENTS 5,523,058 A    6/1996  Umemura et al.
5,777,860 A *  7/1998  Halbert ................. B06B 1/0253
                                                       310/316.01
(Continued)

FOREIGN PATENT DOCUMENTS

| WO | WO98/07470 | 2/1998 |
| WO | WO2005/107600 A1 | 11/2005 |
| WO | WO2013/177430 A1 | 11/2013 |

OTHER PUBLICATIONS

Iernetti et al., "Enhancement of high-frequency acoustic cavitation effects by a low-frequency stimulation". Ultrasonics Sonochemistry 4 (1997) 263-268.*
(Continued)

*Primary Examiner* — Katherine L Fernandez
*Assistant Examiner* — Yi-Shan Yang
(74) *Attorney, Agent, or Firm* — Klarquist Sparkman, LLP (57) ABSTRACT

An apparatus and as method for generating ultrasound. The apparatus comprises: a signal generator arranged to generate a driving signal; and an ultrasound transducer arranged to transmit an ultrasound beam in response to the driving signal received from the signal generator. The signal generator is arranged to combine a carrier wave and a modulating wave having a lower frequency than the carrier wave to generate an amplitude modulated driving signal. The ultrasound beam is suitable for inducing cavitation in a human or animal body tissue.

11 Claims, 4 Drawing Sheets

(52) U.S. Cl.
CPC ............... *A61N 2007/0039* (2013.01); *A61N 2007/0052* (2013.01); *A61N 2007/0073* (2013.01); *A61N 2007/0082* (2013.01)

(56) References Cited

U.S. PATENT DOCUMENTS

| | | | | |
|---|---|---|---|---|
| 5,827,204 | A * | 10/1998 | Grandia | A61B 17/2256 601/2 |
| 7,109,789 | B2 * | 9/2006 | Spencer | H03F 3/2171 330/10 |
| 8,057,408 | B2 | 11/2011 | Cain et al. | |
| 2002/0173697 | A1 | 11/2002 | Lenhardt | |
| 2005/0256404 | A1 * | 11/2005 | Sato | A61B 8/481 600/437 |
| 2010/0292684 | A1 * | 11/2010 | Cybulski | A61B 18/14 606/33 |
| 2011/0144545 | A1 * | 6/2011 | Fan | A61N 7/02 601/3 |
| 2011/0213248 | A1 | 9/2011 | Murakami et al. | |
| 2011/0256503 | A1 * | 10/2011 | Fraser | A61C 17/20 433/119 |
| 2012/0234625 | A1 * | 9/2012 | Laugharn, Jr. | G10K 11/28 181/140 |

OTHER PUBLICATIONS

Urban et al., "Modulation of ultrasound to produce multifrequency radiation force". The Journal of the Acoustical Society of America 127, 1228 (2010) pp. 1228-1238. (Year: 2010).*

Maleke et al., "Harmonic motion imaging for focused ultrasound (HMIFU): a fully integrated technique for sonication and monitoring of thermal ablation in tissues". Phys. Med. Biol. 53 (2008) 1773-1793. (Year: 2008).*

International Search Report and Written Opinion of the International Searching Authority, dated Apr. 22, 2015, for corresponding International Application No. PCT/GB2015/050167, 10 pages.

Search and Examination Report from the United Kingdom Intellectual Property Office for corresponding Application No. GB1401345. 2, dated Aug. 15, 2014, 6 pages.

Examination Report from the United Kingdom Intellectual Property Office for corresponding Application No. GB1401345.2, dated Oct. 1, 2014, 2 pages.

Examination Report from the United Kingdom Intellectual Property Office for corresponding Application No. GB1401345.2, dated Apr. 2, 2015, 3 pages.

Gilles et al., "Cavitation Generated by Amplitude Modulated HIFU: Investigation on the Inertial Cavitation Threshold," CP911, 6th International Symposium on Therapeutic Ultrasound, American Institute of Physics, 2007, pp. 171-177.

Iernetti et al., "Enhancement of high-frequency acoustic cavitation effects by a low-frequency stimulation," *Ultrasonics Sonochemistry*, vol. 4, No. 3, pp. 263-268, Jul. 1, 1997.

Urban et al., "Modulation of ultrasound to produce multifrequency radiation force," *J Acoust Soc Am*, vol. 127, No. 3, pp. 1228-1238, Mar. 2010.

"Communication—European Search Report" from the European Patent Office for European Application No. EP15701417.6-1659, dated Jul. 24, 2017, 5 pages.

* cited by examiner

THERAPEUTIC ULTRASOUND APPARATUS AND METHOD

CROSS REFERENCE TO RELATED APPLICATIONS

This is the U.S. National Stage of International Application No. PCT/GB2015/050167, filed Jan. 26, 2015, which in turn claims the benefit of and priority to United Kingdom Patent Application No. 1401345.2, filed Jan. 27, 2014.

This invention relates to an apparatus and method for generating ultrasound. In particular, the present invention relates to a method and apparatus for generating an ultrasound beam configured to induce cavitation. Certain embodiments of the present invention relate to the use of such an ultrasound beam in cavitation therapy.

BACKGROUND

Historically, the treatment of cancer has focussed on surgical treatment to remove the cancerous tumour or chemical or radiological treatments to destroy the tumour. Over the past two decades a new form of cancer treatment using High Intensity Focused Ultrasound (HIFU) has emerged. HIFU is a hyperthermia therapy. It causes thermal ablation of the treated tissue by focusing the high intensity ultrasound beam onto the diseased tissue. The energy from the beam at the focus causes the tissue to rapidly heat up (within a few seconds). The result is thermally necrosed tissue and immediate cell death. HIFU techniques are limited in their application due to the difficult in precisely controlling the thermal heating. In particular, thermal damage to surrounding tissue is common. A partial solution is to reduce the size of the focus to produce smaller lesions, though this can result in a lengthy treatment to progressively destroy a large volume of tissue.

Cavitation is the formation of vapour cavities in a liquid: small, liquid-free zones (which may be referred to as bubbles or voids) that are the consequence of forces acting upon the liquid. Cavitation is a well-known phenomenon that usually occurs when a liquid is subjected to rapid changes of pressure: cavitation occurs at locations where the pressure is relatively low. When subjected to higher pressure, the voids implode. This implosion can generate an intense shockwave that propagates through the surrounding liquid. This process of cavity formation and collapse may also be referred to as inertial cavitation, and the resulting shockwave can cause damage to solid objects within the liquid. For this reason, cavitation is usually regarded as undesirable when it occurs in man-made objects such as control valves, pumps, propellers and impellers. Cavitation is also a naturally occurring phenomenon, for instance in the strikes of mantis shrimps and pistol shrimps, as well as in the vascular tissues of plants.

During HIFU treatment, acoustic cavitation may occur as a secondary effect, at the focus of the ultrasound beam. Specifically, if the power of the ultrasonic wave is higher than the cavitation threshold of the liquid, cavitation occurs in the negative (rarefaction) part of the sonic wave and the cavities implode in the positive (compression) part of the sonic wave. Since the shock waves formed by collapse of the voids are strong enough to cause significant damage to adjacent tissue, cavitation is usually undesirable in HIFU treatment because the onset of cavitation and the resulting tissue damage can be unpredictable. However, if cavitation generation and collapse through the application of ultrasound can be controlled, it could allow for an effective method of causing tissue damage by fractionation.

Figure 1:
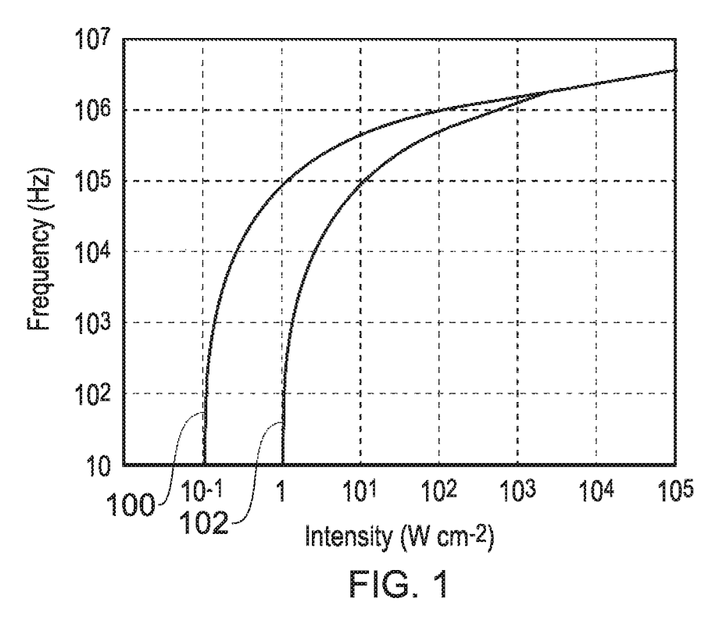
FIG. 1 illustrates variation of the cavitation threshold of a liquid with acoustic frequency.

Cavitation occurs if the fluid pressure is lowered below its vapour pressure. Other physical parameters contributing to the cavitation threshold are liquid temperature and level of impurities including dissolved gases. For cavitation induced through the application of sound or ultrasound, the frequency of the sonic wave (Hz) is a factor, along with the intensity of the sonic wave (W.cm$^{-2}$). The sonic intensity and the frequency affect the minimum pressure generated in the rarefaction portion of the sonic wave, and thus whether cavitation occurs. The lower the frequency of the sonic wave, the lower the cavitation threshold. Referring to FIG. 1, this illustrates for relationship between frequency and intensity for aerated water (line 100) and air-free water (line 102). It will be seen that the intensity required to induce cavitation increases rapidly above $10^4$ to $10^5$ Hz. The cavitation threshold within body tissue varies from patient to patient and between different types of body tissue.

For effective cavitation therapy through the application of ultrasound it is essential to control the generation of cavities, both temporally and spatially. It is further desirable to use low acoustic intensities to generate the cavities, in order to minimise uncontrolled thermal necrosis of surrounding tissue and the associated pain to the patient. Moreover, tissue absorption of ultrasound energy is frequency dependent: less energy is absorbed at lower frequencies. While low frequency acoustic beams would allow the use of low intensities, as is evident from FIG. 1, the focal volume is large which makes it difficult to achieve conformal treatment. A large focal volume does not allow beam focusing near blood vessels, nerves, or sensitive organs. Conversely, at higher frequencies, which allow for a narrower focus and hence closer spatial control of the cavities, the sonic intensity required would cause undesired thermal necrosis, which could dwarf the desired cavitation effect.

It is known to generate therapeutic cavitation through the application of a pulsed ultrasonic beam. For instance, U.S. Pat. No. 8,057,408-B2 describes pulsed cavitation ultrasound therapy in which a pulsed ultrasound is used to generate a pulsed acoustic pressure waveform. FIG. 19 shows a representative graph of 11 cycles, each cycle comprise a short pulse of 15 cycles of high energy ultrasound waves. However, there are known drawbacks to generating cavitation through pulsed ultrasound. In particular, current HIFU transducers operate in the range 750 KHz up to 4 MHz. At such high frequencies the cavitation threshold is high which requires high acoustic intensities for cavitation generation. Current methods using pulsed rate ultrasound require higher intensities than HIFU to generate cavitation. Indeed, the peak negative pressure is twice that used in HIFU thermal ablation. This increases the risk of healthy tissue damage causing pain and the risk of internal organ injury. Moreover, pulsed ultrasound at high intensity levels require a large ultrasound transducer, efficient cooling, and prolongs the treatment time, which causes more inconvenience to the patient.

Figure 2:
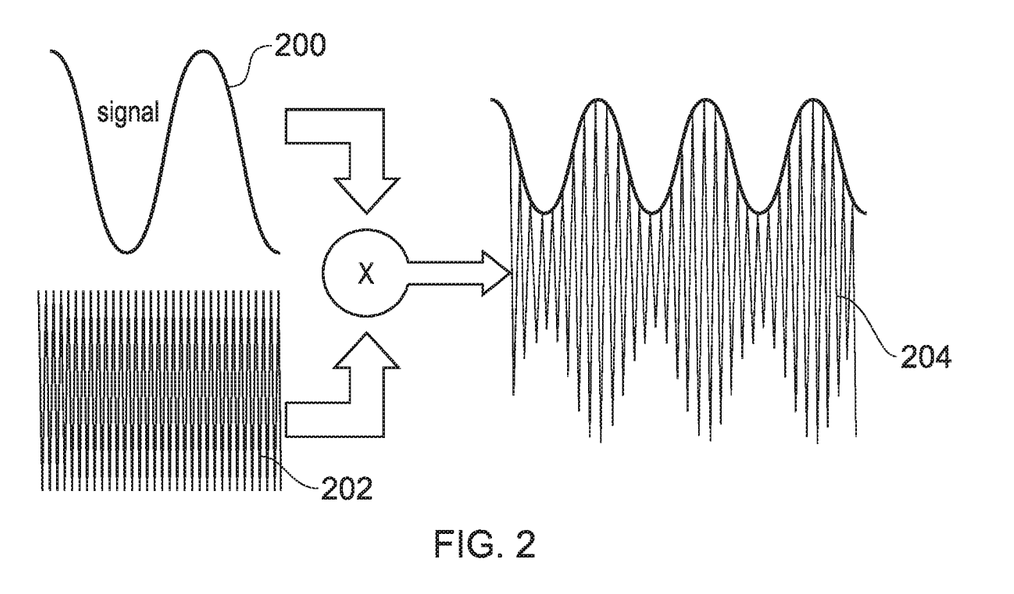
FIG. 2 schematically illustrates amplitude modulation of an ultrasound driving signal in accordance with an embodiment of the present invention.

WO-2005/107600-A1 describes an enhancement to therapeutic ultrasonic cavitation in which two or more ultrasound transducers driven with a common drive signal generate separate ultrasound signals that meet at a common focus to cause cavitation. To cause cavity implosion the drive signals supplied to each transducer are altered, for instance such that one is set to 1.00 MHz and one is set to 1.01 MHz. The resulting non-identical ultrasound signals interfere at the common focus to cause a resulting ultrasonic pressure field that varies at a relatively low pressure, on the order of several Hz up to several tens of KHz. Alternatively, both drive signals may be supplied to the same transducer to produce an ultrasonic wave having a frequency of approximately 1 MHz with a varying phase and varying amplitude, as shown in FIG. 2. A similar mixing of two frequencies is described in Gilles B. et al, "Cavitation Generated by Amplitude Modulated HIFU: Investigation on the Inertial Cavitation Threshold", 6$^{th}$ International Symposium on Therapeutic Ultrasound, American Institute of Physics, 2007. For instance, this discloses "dichromatic excitation" through a summation of two sine waves of slightly different frequencies $f_1$—536.5 KHz and $f_2$—569.5 KHz. This approach may be referred to as frequency mixing. It is not possible to closely control or shape the varying amplitude following this approach. Specifically, frequency mixing can only give a single beat frequency affecting the amplitude, which may not be the desired result.

BRIEF SUMMARY OF THE DISCLOSURE

It is an aim of certain embodiments of the present invention to provide improved methods and apparatuses for generating ultrasound for use in cavitation therapy. In particular, embodiments of the presentation make use of Amplitude Modulation (AM) to achieve cavitation generation using a high frequency focused ultrasound transducer. Advantageously, this allows the amplitude of the ultrasound to be shaped at will through control of the modulating signal. A further advantage is that high frequency focused ultrasound transducers are well known and relatively low cost items.

According to a first aspect of the present invention there is provided an apparatus for generating ultrasound, the apparatus comprising: a signal generator arranged to generate a driving signal; and an ultrasound transducer arranged to transmit an ultrasound beam in response to the driving signal received from the signal generator; wherein the signal generator is arranged to combine a carrier wave and a modulating wave having a lower frequency than the carrier wave to generate an amplitude modulated driving signal; and wherein the ultrasound beam is suitable for inducing cavitation in a human or animal body tissue.

Preferably, the carrier wave is between 0.5 MHz and 5 MHz and the modulating wave is between 1 KHz and 100 KHz.

The ultrasound transducer may be focussed; and wherein the signal generator is arranged to cause the ultrasound transducer to generate an ultrasound beam which is suitable for inducing cavitation within a focal region of the transducer.

The ultrasound transducer may be arranged to produce a continuous wave ultrasound beam.

The signal generator may be controllable to generate a driving signal which is arranged to cause the ultrasound transducer to generate an ultrasound beam with a variable acoustic intensity; generate a driving signal having a variable degree of amplitude modulation; generate a driving signal which is symmetrically or asymmetrically modulated; generate a driving signal which is amplitude modulated with a variable modulation frequency; or select an output bandwidth of the signal generator to generate a driving signal selectively including at least one of the carrier wave frequency, a lower side band and an upper sideband.

The apparatus may further comprise at least one ultrasound imaging probe arranged to generate a signal indicating a current location of cavitation.

The apparatus may further comprise: a second ultrasound transducer arranged to transmit a second ultrasound beam which is at a lower frequency than the carrier wave, the second ultrasound beam having a lower acoustic intensity than the first ultrasound beam being suitable for assisting in maintaining cavitation in a human or animal body tissue induced by the first ultrasound beam.

According to a second aspect of the present invention there is provided a method for generating ultrasound, the method comprising: generating, by a signal generator, a driving signal; and transmitting, by an ultrasound transducer, an ultrasound beam in response to the driving signal received from the signal generator; wherein generating a driving signal comprises combining a carrier wave and a modulating wave having a lower frequency than the carrier wave to generate an amplitude modulated driving signal; and wherein the ultrasound beam is suitable for inducing cavitation in a human or animal body tissue.

Preferably, the carrier wave is between 0.5 MHz and 5 MHz and the modulating wave is between 1 KHz and 100 KHz.

The ultrasound transducer may be focussed; and the ultrasound beam may be suitable for inducing cavitation within a focal region of the transducer.

The ultrasound beam may be a continuous wave ultrasound beam.

The method may further comprise controlling the signal generator to: generate a driving signal which is arranged to cause the ultrasound transducer to generate an ultrasound beam with a variable acoustic intensity; generate a driving signal having a variable degree of amplitude modulation; generate a driving signal which is symmetrically or asymmetrically modulated; generate a driving signal which is amplitude modulated with a variable modulation frequency; or select an output bandwidth of the signal generator to generate a driving signal selectively including at least one of the carrier wave frequency, a lower side band and an upper sideband.

The method may further comprise: operating at least one ultrasound imaging probe to generate a signal indicating a current location of cavitation.

The method may further comprise: transmitting, by a second ultrasound transducer, a second ultrasound beam which is at a lower frequency than the carrier wave, the second ultrasound beam being suitable for assisting in maintaining cavitation in a human or animal body tissue induced by the first ultrasound beam.

According to a third aspect of the present invention there is provided a therapeutic method comprising: generating ultrasound according to the method described above; wherein the ultrasound transducer is positioned proximal to a portion of a human or animal body to cause cavitation in a desired body tissue.

BRIEF DESCRIPTION OF THE DRAWINGS

Embodiments of the invention are further described hereinafter with reference to the accompanying drawings, in which.

DETAILED DESCRIPTION

In accordance with certain embodiments of the present invention there is provided an apparatus which uses an amplitude modulated high intensity focused ultrasound beam to generate inertial cavitation at the focal region where the ultrasound intensity is maximised. Amplitude modulation of the HIFU beam is used to control the cavitation generation and to direct the destructive effects of imploding cavities. Where cavity implosion occurs at a liquid/tissue interface this causes damage to the adjacent tissue. The damage is caused by the implosion of the cavity and the release of a large amount of energy acquired from the ultrasound beam and stored inside the cavities over repeated cycles of the HIFU wave. Specifically, tissue damage is caused by water jetting which causes tissue fractionation at a micron level. To generate the amplitude modulated HIFU beam, a carrier wave is used. The frequency of the carrier wave may typically be between 0.5 MHz and 5 MHz.

The modulating signal is at a low frequency relative to the carrier wave. Typically, the modulating signal may be between 1 KHz and 100 KHz. The low frequency modulating signal lowers the cavitation generation threshold as shown in FIG. 1. This allowing the generation of cavities at lower acoustic intensities. The precise range of acoustic intensities will vary according to a large number of factors, as discussed in the background section above. Low acoustic intensities minimize the risk of injury and CW mode reduces treatment time. For example, if the ultrasound wave is amplitude modulated at 10 KHz, as shown in FIG. 1 the cavitation threshold is around 1 W.cm$^{-2}$ compared to about 500 W. cm$^{-2}$ at atypical HIFU frequency of 1 MHz. Amplitude modulation also allows the delivery of the energy in a Continuous Wave (CVV) ultrasound mode, which can reduce treatment times and discomfort to the patient due to large variation in acoustic intensity.

The amplitude modulated HIFU beam allows control of the amount of stored energy in the cavities before cavity implosion. As shown in FIG. 2, the amplitude modulation comprises a low frequency signal (modulating wave signal 200) used to modulate the amplitude of a higher frequency signal (carrier wave signal 202) to generate a modulated carrier wave 204. The modulated carrier wave comprises a drive signal supplied to an ultrasound transducer to generate an amplitude modulated ultrasound beam. Advantageously, amplitude modulation through the use of a modulating wave 200 allows for fine control of the shape of the modulated carrier wave 204, which is not possible through the frequency mixing approach demonstrated in the prior art. The present inventor has realised that this control may be used to optimise the energy released by imploding cavities as well as the temporal and spatial control of cavitation therapy.

The result of amplitude modulation is an ultrasound wave that changes its amplitude periodically at a rate equal to the frequency of the lower frequency modulating signal. If an amplitude modulated ultrasound beam is focused at a distance from the generating source in water a cloud of cavities/bubbles will form at the focal region. The bubble cloud remains confined to this region because the ultrasound intensity is at a maximum in the focal region. As noted above, a prime consideration for cavitation therapy is the ability to closely control the spatial distribution of cavitation.

By amplitude modulating the output from a high frequency ultrasound transducer, the ability of such a transducer to provide accurate focussing and a well-defined focal geometry is retained. At the same time, due to the relatively low frequency amplitude modulation, the acoustic intensity to generate cavitation is much reduced, which reduces the risk of thermal injury. Alternatively, the acoustic intensity may be increased in order to cause a desired amount of thermal ablation in addition to the tissue fractionation due to cavitation. In accordance with certain embodiments of the invention the relative proportions of thermal ablation and tissue fractionation may be controlled according to clinical indications or surgeon preference.

In certain embodiments the degree of amplitude modulation (which, for instance, could be defined as the proportional change between peak and minimum amplitude) can be controlled in addition to or in place of adjusting the frequency of the modulating signal. A lower degree of amplitude modulation favours thermal ablation over tissue fractionation due to cavitation. The degree of amplitude modulation may vary between 0%, which corresponds to only thermal effects and 100% which corresponds to a maximised cavitation effect.

The modulating signal 200 in FIG. 2 is generally sinusoidal. However, it will be appreciated that this is not necessarily the case and the modulating signal may be any desired (and reproducible) signal. For instance, referring to FIG. 3, this schematically illustrates amplitude modulation using an arbitrary modulating signal in accordance with an embodiment of the present invention. Specifically, carrier wave 300 is amplitude modulated by an arbitrary modulating wave 302 to produce a high frequency amplitude modulated signal 304. The flexibility to shape the modulating signal allows the cavitation therapy to be tailored to the tumour tissue stiffness. Tissue stiffness can very between tumours and between different regions of the same tumour. For instance, calcified regions within a tumour are harder than soft tissue. In treatment planning, the clinician can select the appropriate modulating signal shape to tailor the treatment for inhomogeneous tumour tissue. The spatial distribution of the cavitation is determined by the focal region of the ultrasound transducer. The geometry of the focal region is determined by the curvature of the focusing lens and by the frequency of the carrier wave. Typically, the frequency of the carrier wave is determined by the resonance frequency of the HIFU transducer which does not change. Within the focal region the clinician can shape the carrier to achieve treatment of inhomogeneous tumour tissue. By shaping the modulating signal such that the frequency of the modulating (envelope) signal changes, and/or such that the degree (percentage) of modulation changes, the cavitation threshold can be altered over time to accommodate different tissue stiffness. For example a modulating signal of 1 KHz and 100% modulation requires less carrier intensity to generate cavitation than 10 KHz at the same 100% modulation.

Figure 3:
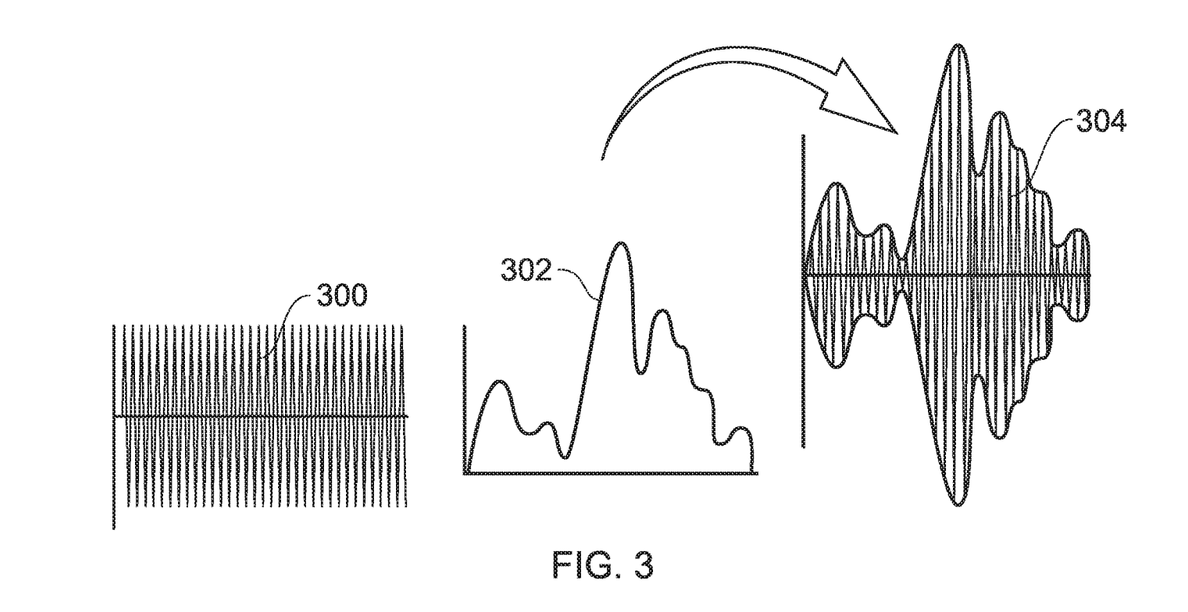
FIG. 3 schematically illustrates amplitude modulation using an arbitrary modulating signal in accordance with an embodiment of the present invention.
Figure 4:
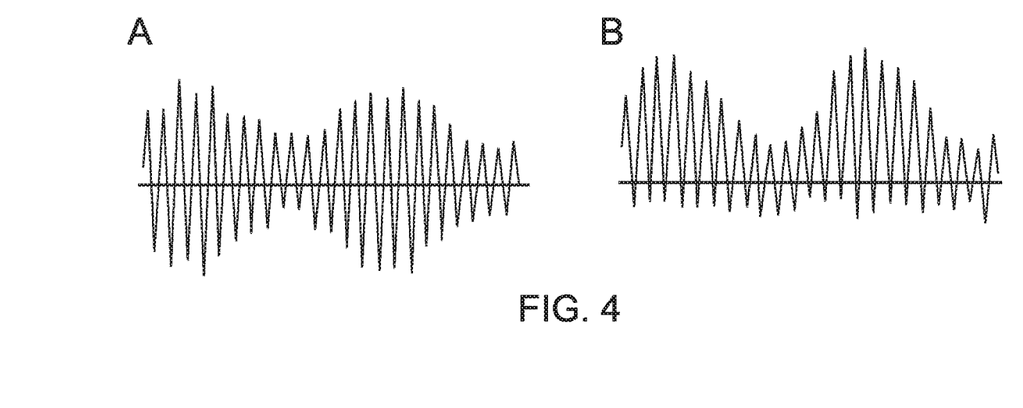
FIG. 4 illustrates (A) symmetrical amplitude modulation and (B) asymmetrical amplitude modulation.

FIGS. 2 and 3 show symmetric ultrasound modulation. However, in certain embodiments of the invention asymmetrical modulation can be used. Referring to FIG. 4, this illustrates the difference between symmetrical amplitude modulation (part A) and asymmetrical amplitude modulation (part B). Specifically, the positive and negative parts of the signal are no longer equal. Advantageously, asymmetry can allow for control over the relative rarefaction and compression pressures. For example, asymmetry can allow for higher rarefaction pressure and lower compression pressure while keeping the total energy within one cycle to remain the same as for a symmetrical signal. The initiation of cavitation may be achieved at lower overall energy levels, for instance by using an asymmetrical signal to provide for larger rarefaction. Additionally, symmetrical signals can allow cavities to grow in the ultrasound field by a process called rectified diffusion. Asymmetry biased towards compression forces cavities to implode faster than is the case for symmetrical signal. In certain embodiments asymmetrical modulation may be used in which the bias between rarefaction and compression varies over time. This can allow for defined periods of cavitation generation and cavitation implosion.

Figure 5:
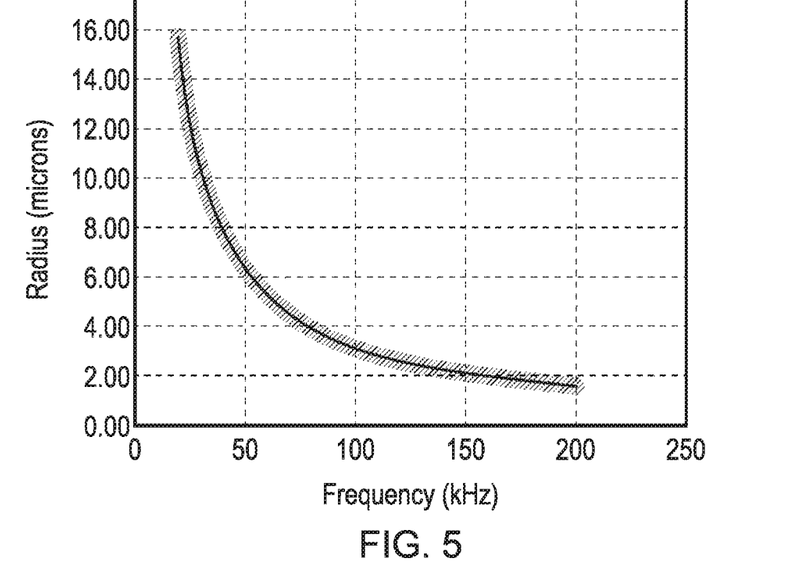
FIG. 5 illustrates the relationship between cavitation radius (microns) and driving frequency (KHz)

A further advantage of using amplitude modulation is that the cavity (bubble) size varies with the modulating frequency, which in a typical embodiment can be controlled between 1 KHz and 100 KHz. FIG. 5 illustrates the relationship between cavitation radius (microns) and driving frequency (KHz). Advantageously, a larger cavity stores a larger amount of energy absorbed from the ultrasound beam, and so causes a larger shockwave on implosion. Consequently, the intensity of cavitation therapy can be adjusted according to clinical indications, such as tissue type, or surgeon preference. In particular, cavity size control enables precise conformal treatment close to blood vessels, nerves and sensitive organs.

Figure 6:
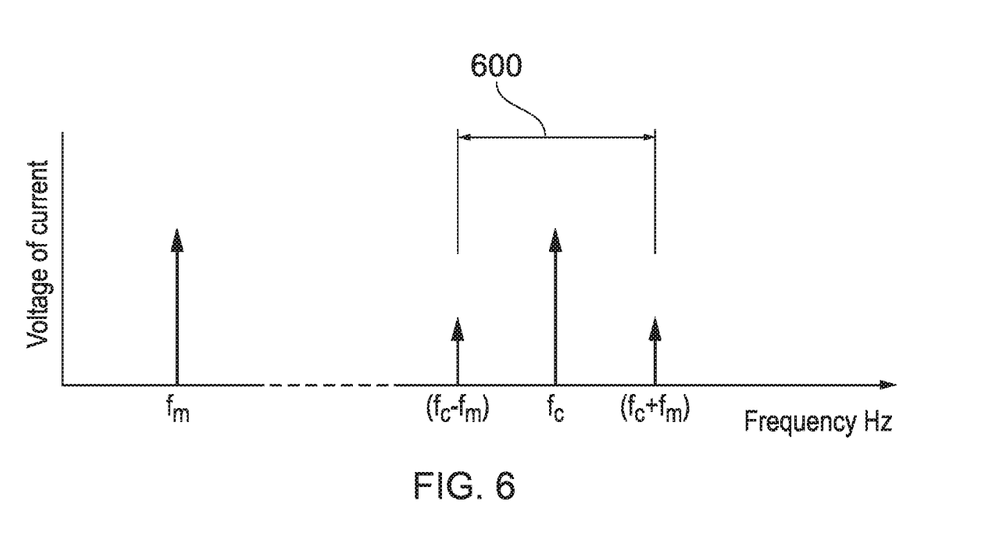
FIG. 6 illustrates a frequency graph showing the effect of amplitude modulation of a carrier wave.

A further advantage of using amplitude modulation is that by controlling the bandwidth of the driving signal the intensity of cavitation generation can be adjusted. FIG. 6 illustrates a frequency graph showing the effect of amplitude modulation of a carrier wave. The carrier signal $f_c$ and the modulating wave $f_m$ are shown. Amplitude modulation causes the generation of upper and lower side frequencies $(f_c+F_m)$ and $(f_c-F_m)$ which are themselves frequency modulated. To transmit the fully amplitude modulated drive signal the bandwidth of the drive signal must be selected to include both side frequencies, as shown by bandwidth 600. Alternatively, the operator may adjust the bandwidth to select only the carrier wave $f_c$ to maximise the thermal effect of the ultrasound beam and minimise cavitation effects. A further alternative is for the operator to select one side frequency (and to optionally suppress the carrier wave), which results in low intensity cavitation generation. If the lower side frequency is selected then there is no loss of transducer efficiency as the lower side band operates within the range of resonance frequency of a HIFU transducer.

Figure 7:
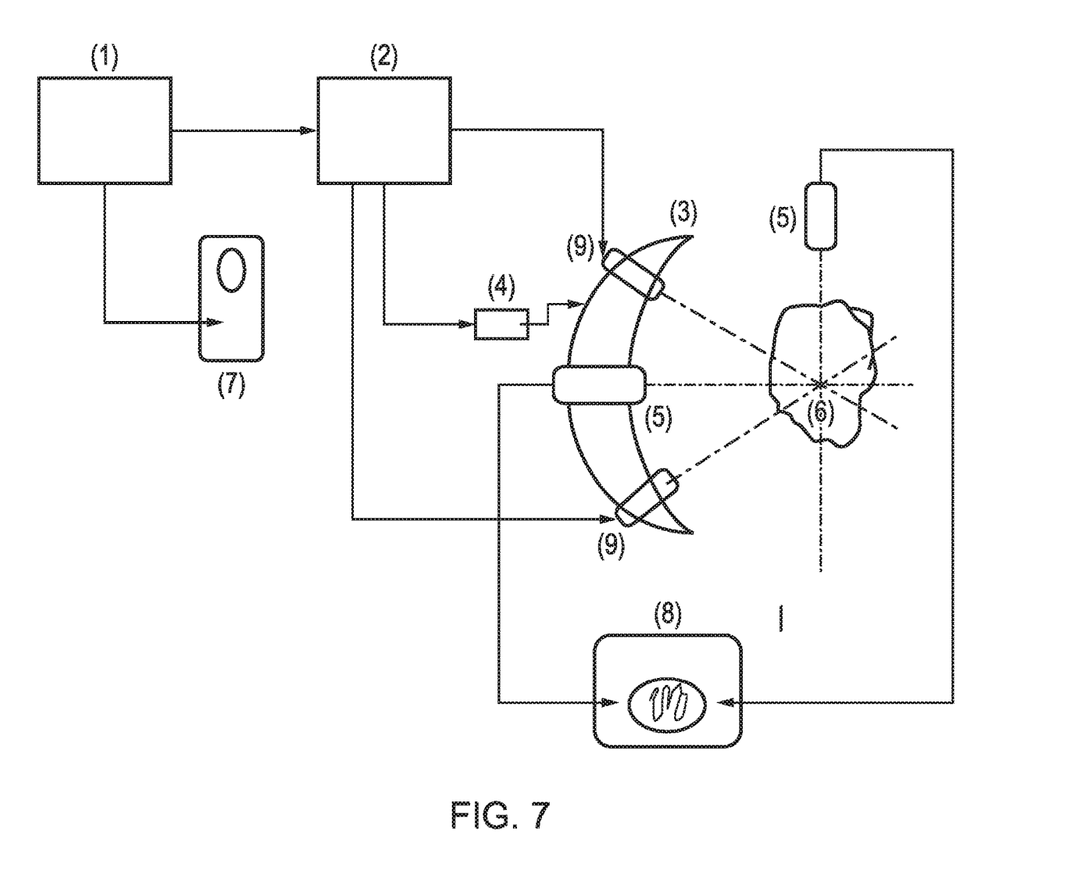
FIG. 7 schematically illustrates an apparatus for generating ultrasound in accordance with an embodiment of the present invention.

Referring now to FIG. 7, this illustrates an apparatus in accordance with an embodiment of the present invention for use in ultrasound therapy. Specifically, FIG. 7 shows an ultrasound cavitation generation and monitoring system. The apparatus comprises a signal generator 1, also referred to as a function generator, arranged to generate an amplitude modulated ultrasound drive signal as shown in FIGS. 2 to 4 through the combination of a modulating wave and a carrier wave. The signal generator 1 may comprise a computer arranged to be programmed to generate a desired drive signal, or alternatively it may be under the control of the operator. The signal generator 1 supplies the drive signal to a Radio Frequency (RF) amplifier 2 to amplify the drive signal. The RF amplifier 2 may contain two separate amplifiers: a low frequency amplifier for supplying a low frequency amplified drive signal to low frequency ultrasound transducers (discussed below) in addition to a high frequency amplifier for supplying a high frequency amplified drive signal to a HIFU transducer 3.

The HIFU transducer may typically be a single crystal or a multi-crystal phased array transducer. The drive signal may be supplied to HIFU transducer 3 through an impedance matching circuit 4 in certain embodiments to minimise signal losses due to reflections of the drive signal. The HIFU transducer 3 may advantageously be a curved ultrasound transducer array to focus the ultrasound beam on a focal point within a target tissue 6 (at the point where cavitation therapy is desired). However, the present invention is not limited to this. Other techniques for producing a focussed ultrasound beam will be well known to the skilled person, for instance the use of multiple transducers with intersecting beam paths. A pair of low frequency (1-100 KHz) focused ultrasound transducers 9 are provided in certain embodiments and used to maintain cavitation after initiation by the HIFU transducer 3. The low frequency transducers may typically be single crystal focused probes. It will be appreciated that alternatively there may be a single low frequency transducer, or more than two. This is advantageous for treating large benign tumours at lower intensities and minimal thermal effect in bulk tissue fractionation where accuracy is not a problem such as the case in benign tumours. Advantageously, this can speed up the process of tissue fractionation at lower acoustic intensities, reduce treatment time and is useful in treating large tumours such as uterine fibroids.

Two ultrasound imaging probes 5 are provided in certain embodiments for imaging the cavitation field during therapy, which can help with alignment and for monitoring progress. Of course, there may only be a single imaging probe 5, but it is desirable to provide a pair, for instance at 90° to one another, to image the cavitation field in two intersecting planes. FIG. 7 shows one imaging probe 5 being collocated with the HIFU transducer, which allows the focal point of the HIFU transducer to be positioned onto the target tissue within a plane perpendicular to the centre of the HIFU beam path. The second imaging probe allows the focal point of the HIFU transducer to be positioned along an axis extending along the centre of the HIFU beam path. This imaging probe can rotate independent of the HIFU probe 3, from 0 to 90° along the HIFU long beam axis. This allows creation of a 3D image of the tumour and volumetric visualisation of the treated zone. The imaging probes may be passive, in that they receive reflected ultrasound waves from the HIFU transducer 3, or they may be active (B-mode and Doppler). Due to the liquid/gas interface at a cavity, the cavitation field is readily imaged. Real-time ultrasound monitoring allows for real-time adjustments to be made to the cavitation treatment to ensure close control of tissue fractionation within the boundaries of a tumour. It also allows for rapid location of the ultrasound beam within the tissue to be treated. The imaging probes 5 may be linear, curve-linear or phased array probes. Their frequency may typically vary between 3 MHz and 14 MHz depending on desired penetration depth and image resolution. The imaging probes 5 are coupled to an ultrasound scanner 8 for displaying an ultrasound image (B-mode and Doppler). Oscilloscope 7 may also be provided for viewing the amplitude modulated drive signal.

In a therapeutic method for generating cavitation (for instance to destroy a tumour) the apparatus described above can be used to generate ultrasound beams (imaging and therapy) directed from outside the body (totally non-invasive). For treatment of certain conditions the ultrasound beams may be directed from inside a body cavity (for instance, the rectum or vagina). Such a minimally invasive approach may be used to treat certain indications such as in rectal, prostate or vaginal cancers.

Throughout the description and claims of this specification, the words "comprise" and "contain" and variations of the words, for example "comprising" and "comprises", means "including but not limited to", and is not intended to (and does not) exclude other components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers or characteristics described in conjunction with a particular aspect, embodiment or example of the invention are to be understood to be applicable to any other aspect, embodiment or example described herein unless incompatible therewith.

It will be also be appreciated that, throughout the description and claims of this specification, language in the general form of "X for Y" (where Y is some action, activity or step and X is some means for carrying out that action, activity or step) encompasses means X adapted or arranged specifically, but not exclusively, to do Y.

The invention claimed is:

1. An apparatus for generating ultrasound, the apparatus comprising:
   a signal generator arranged to generate a driving signal; and
   a focused ultrasound transducer arranged to transmit a focused ultrasound beam in response to the driving signal received from the signal generator;
   wherein the signal generator is arranged to combine a carrier wave and a modulating wave having a lower frequency than the carrier wave via Amplitude Modulation (AM) to generate an amplitude modulated driving signal in which the amplitude of the carrier wave is modulated by the modulating wave by multiplying the carrier wave with the modulating wave;
   wherein the focused ultrasound beam is suitable for inducing inertial cavitation in a human or animal body tissue within a focal region of the focused ultrasound transducer; and
   wherein the carrier wave has a carrier wave frequency between 0.5 MHz and 5 MHz and the modulating wave has a modulating wave frequency between 1 KHz and 100 KHz.

2. The apparatus according to claim 1, wherein the focused ultrasound beam is a continuous wave ultrasound beam.

3. The apparatus according to claim 1, wherein the signal generator is controllable to:
   generate the driving signal such that the driving signal is arranged to cause the focused ultrasound transducer to generate the focused ultrasound beam such that the focused ultrasound beam has a variable acoustic intensity;
   generate the driving signal such that the driving signal has a variable degree of amplitude modulation;
   generate the driving signal such that the driving signal is symmetrically or asymmetrically modulated;
   generate the driving signal such that the driving signal is amplitude modulated with a variable modulation frequency; or
   select an output bandwidth of the signal generator to generate the driving signal such that the driving signal selectively includes at least one of the carrier wave frequency, a lower side band and an upper sideband.

4. The apparatus according to claim 1, further comprising: at least one ultrasound imaging probe arranged to generate a signal indicating a current location of the inertial cavitation.

5. The apparatus according to claim 1, wherein the focused ultrasound beam comprises a first ultrasound beam and the apparatus further comprises: a second ultrasound transducer arranged to transmit a second ultrasound beam that is at a lower frequency than the carrier wave, the second ultrasound beam having a lower acoustic intensity than the first ultrasound beam, wherein the second ultrasound beam is suitable for assisting in maintaining the inertial cavitation in the human or animal body tissue induced by the first ultrasound beam.

6. A method for generating ultrasound, the method comprising:
   generating, by a signal generator, a driving signal; and
   transmitting, by a focused ultrasound transducer, a focused ultrasound beam in response to the driving signal received from the signal generator;
   wherein generating the driving signal comprises combining a carrier wave and a modulating wave having a lower frequency than the carrier wave via Amplitude Modulation (AM) to generate an amplitude modulated driving signal in which the amplitude of the carrier wave is modulated by the modulating wave by multiplying the carrier wave with the modulating wave;
   wherein the focused ultrasound beam is suitable for inducing inertial cavitation in a human or animal body tissue within a focal region of the focused ultrasound transducer; and;
   wherein the carrier wave has a carrier wave frequency between 0.5 MHz and 5 MHz and the modulating wave has a modulating wave frequency between 1 KHz and 100 KHz.

7. The method according to claim 6, wherein the focused ultrasound beam is a continuous wave ultrasound beam.

8. The method according to claim 6, further comprising controlling the signal generator to:
   generate the driving signal such that the driving signal is arranged to cause the focused ultrasound transducer to generate the focused ultrasound beam such that the driving signal has a variable acoustic intensity;
   generate the driving signal such that the driving signal has a variable degree of amplitude modulation; generate the driving signal such that it is symmetrically or asymmetrically modulated;
   generate the driving signal such that the driving signal is amplitude modulated with a variable modulation frequency; or select an output bandwidth of the signal generator to generate the driving signal such that the driving signal selectively includes at least one of the carrier wave frequency, a lower side band and an upper sideband.

9. The method according to claim 6, further comprising: operating at least one ultrasound imaging probe to generate a signal indicating a current location of the inertial cavitation.

10. The method according to claim 6, wherein the focused ultrasound beam comprises a first ultrasound beam and the method further comprises: transmitting, by a second ultrasound transducer, a second ultrasound beam that is at a lower frequency than the carrier wave, the second ultrasound beam being suitable for assisting in maintaining the inertial cavitation in the human or animal body tissue induced by the first ultrasound beam.

11. The method according to claim 6, wherein the focused ultrasound transducer is positioned proximal to a portion of the human or animal body to cause the inertial cavitation in a desired body tissue.

\* \* \* \* \*